US00PP09518P

United States Patent [19]

Polys

[11] Patent Number: Plant 9,518

[45] Date of Patent: Apr. 23, 1996

[54] CHRYSANTHEMUM PLANT NAMED 'APRICOT BLUSH'

[75] Inventor: Susan M. Polys, Salinas, Calif.

[73] Assignee: Yoder Brothers, Inc., Barberton, Ohio

[21] Appl. No.: 331,860

[22] Filed: Nov. 1, 1994

[51] Int. Cl.[6] ..... A01H 5/00

[52] U.S. Cl. ..... Plt./82.3

[58] Field of Search ..... Plt./74.1, 82.3, Plt./82.4

[56] References Cited

U.S. PATENT DOCUMENTS

| | | | |
|---|---|---|---|
| P.P. 7,985 | 9/1992 | VandenBerg | Plt./82.4 |
| 4,616,099 | 10/1986 | Sparkes | 47/58 |

OTHER PUBLICATIONS

Broertjes et al., 1980, "A mutant of a mutant of a . . . Irradiation of progressive radiation–induced mutants in a mutation breeding programme with *C. morifolium*", Euphytica, 29:525–530.

Gosling, ed., 1979, "The Chrysanthemum Manual–6th edition", The National Chrysanthemum Society, London, Essex Telegraph Press, Ltd., London, pp. 329–336.

Broetjes, et al., 1978, "Application of Mutation Breeding Methods in the Improvement of Vegetatively Propagated Crops", Elsevier Sci. Pub. Co., New York, pp. 162–175.

Searle, et al., 1968, "Chysanthemums the Year Round–3rd edition", Blanford Press, London, pp. 27–29, 320–327.

Chan, 1966, "Chrysanthemum and rose mutations induced by X–rays", Am. Soc. Hort. Sci. Proc., vol. 88, pp. 613–620.

Broertjes, 1966, "Mutation breeding of Chrysanthemums", Euphytica, 15:156–162.

Dowrick, et al., 1966, "The induction of mutations in chrysanthemum using x– and gamma radiation", Euphytica, 15:204–210.

*Primary Examiner*—Howard J. Locker

*Attorney, Agent, or Firm*—Foley & Lardner

[57] ABSTRACT

A chrysanthemum plant named Apricot Blush particularly characterized by its flat capitulum form; daisy capitulum type; orange-red ray floret color; diameter across face of capitulum of 127 to 140 mm when fully opened, when grown as a pinched disbudded pot mum; photoperiodic flowering response to short days of 53 to 60 days; plant height, with 20 to 22 long days after sticking unrooted cuttings and with 1 to 2 applications of 250 ppm B-9 SP, ranges from 23 to 28 cm when grown as a pinched pot mum with 4 cuttings in a 15 cm pot; branching pattern is semi-spreading, each plant having 3 to 5 laterals after pinch; and recommended as disbudded pot mum.

1 Drawing Sheet

The present invention comprises a new and distinct cultivar of Chrysanthemum, botanically known as *Dendranthema grandiflora*, and referred to by the cultivar name Apricot Blush.

Apricot Blush, identified as 4787 (86-627K02), is a product of a mutation induction program. The new cultivar was discovered and selected by Susan M. Polys on Nov. 25, 1992 in a controlled environment in Salinas, Calif., as one flowering plant within a flowering block established as rooted cuttings from stock plants which had been exposed as unrooted cuttings to an X-ray source of 1750 rads in Fort Myers, Fla., on Jun. 11, 1992. The irradiated parent cultivar was the cultivar identified as Coral Blush, disclosed in pending application Ser. No. 08/296,466, and described as a disbud daisy pot mum with a flat capitulum form; coral-orange ray floret color; diameter across face of capitulum of 114 to 121 mm when fully opened, when grown as a pinched disbudded pot mum; flowering response period of 51 to 55 days after start of short days; plant height, with 20 to 22 long days after sticking unrooted cuttings and with 1 to 2 applications of 2500 ppm B-9 SP of 23 to 30 cm when grown as a pinched pot mum in a 15 cm pot; semi-spreading branching pattern, with 3 to 5 laterals after pinch; and recommended as a disbudded pot mum.

The irradiation program resulting in Apricot Blush had as its primary objective the expansion of color ranges of the parent cultivar. The irradiation program comprised irradiating cuttings of the parent cultivar at irradiation levels of 1500, 1750 and 2000 rads. A total of 1699 cuttings harvested from a total of 225 irradiated plants were planted on Sep. 21, 1992. Of these, 5 initial selections were made, which selections were then revegetated and reflowered. Three consecutive flowerings resulted in discarding 4 of the original 5 selections on Aug. 3, 1993. Continued flowering trials resulted in the decision to introduce the one remaining selection as Apricot Blush.

The first act of asexual reproduction of Apricot Blush was accomplished when vegetative cuttings were taken from the initial selection in January 1993 in a controlled environment in Salinas, Calif., by technicians working under supervision of Susan M. Polys.

Horticultural examination of controlled flowerings of successive plantings has shown that the unique combination of characteristics as herein disclosed for Apricot Blush are firmly fixed and are retained through successive generations of asexual reproduction.

Apricot Blush has not been observed under all possible environmental conditions. The phenotype may vary significantly with variations in environment such as temperature, light intensity and daylength, without, however, any variance in genotype.

The following observations, measurements and comparisons describe plants grown in Salinas, Calif. under greenhouse conditions which approximate those generally used in commercial greenhouse practice.

The following traits have been repeatedly observed and are determined to be basic characteristics of Apricot Blush, which, in combination, distinguish this Chrysanthemum as a new and distinct cultivar:

1. Flat capitulum form.
2. Daisy capitulum type.
3. Orange-red ray floret color.
4. Diameter across face of capitulum of 127 to 140 mm when fully opened, when grown as a pinched disbudded pot mum.

5. Photoperiodic flowering response to short days of 53 to 60 days.

6. Plant height, with 20 to 22 long days after sticking unrooted cuttings and with 1 to 2 applications of 2500 ppm B-9 SP, ranges from 23 to 28 cm when grown as a pinched pot mum with 4 cuttings in a 15 cm pot.

7. Branching pattern is semi-spreading, each plant having 3 to 5 laterals after pinch.

8. Recommended as disbudded pot mum.

The accompanying photographic drawing is a side view of a potted mum of Apricot Blush, with 4 cuttings in a 15 cm pot, with the colors being as nearly true as possible with illustrations of this type.

Of the commercial cultivars known to the inventor, the most similar in comparison to Apricot Blush is the parent cultivar Coral Blush. All traits of Apricot Blush are similar to those of Coral Blush, except for ray floret color and the flowering response to short days. The ray floret color of Apricot Blush is in the orange to orange-red group, while the ray floret color of Coral Blush is in the yellow-orange to orange group. Flowering response to short days of Apricot Blush has been 2 days slower than the flowering response of Coral Blush.

In the following description color references are made to the Royal Horticultural Society Colour Chart. The color values were determined on plant material grown as a pinched spray pot mum in Salinas, Calif. on Mar. 8, 1994.

Classification:

*Botanical.*—*Dendranthema grandiflora* cv Apricot Blush.

*Commercial.*—Flat daisy spray pot mum.

INFLORESCENCE

A. Capitulum:

*Form.*—Flat.

*Type.*—Daisy.

*Diameter across face.*—127 to 140 mm when fully opened.

B. Corolla of ray florets:

*Color (general tonality from a distance of three meters).*—Orange-red.

*Color (upper surface).*—26C, overlaid with 31C to 31D.

*Color (under surface).*—26C.

*Shape.*—Straight, pointed, slightly ribbed.

C. Corolla of disc florets:

*Color (mature).*—7B.

*Color (immature).*—144A to 144B.

D. Reproductive organs:

*Androecium.*—Present on disc florets only; scant pollen.

*Gynoecium.*—Present on both ray and disc florets.

PLANT

A. General appearance:

*Height.*—23 to 28 cm when grown as a pinched pot mum with 20 to 22 long days prior to start of short days, and with 1 to 2 applications of 2500 ppm B-9 SP.

*Branching pattern.*—Semi-spreading, with 3 to 5 laterals after pinch.

B. Foliage:

*Color (upper surface).*—147A.

*Color (under surface).*—147B.

*Shape.*—Moderately lobed and slightly serrated.

I claim:

1. A new and distinct Chrysanthemum plant named Apricot Blush, as described and illustrated.

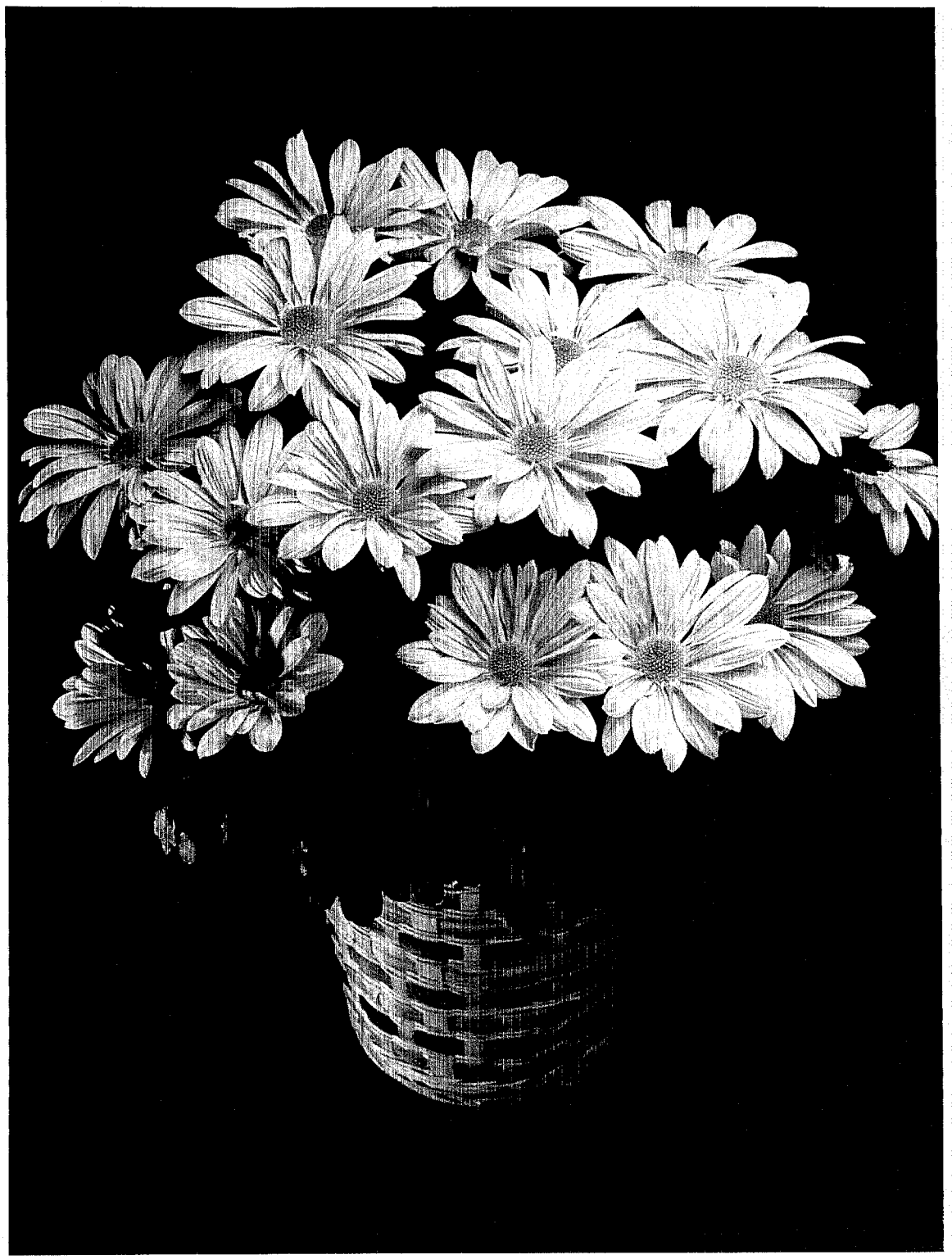

* * * * *